(12) United States Patent
Yamawaki

(10) Patent No.: US 11,160,740 B2
(45) Date of Patent: Nov. 2, 2021

(54) WATER-BASED LIQUID COSMETIC

(71) Applicant: TOKIWA CORPORATION, Nakatsugawa (JP)

(72) Inventor: Yuka Yamawaki, Kawaguchi (JP)

( * ) Notice: Subject to any disclaimer, the term of this patent is extended or adjusted under 35 U.S.C. 154(b) by 0 days.

(21) Appl. No.: 16/655,255

(22) Filed: Oct. 17, 2019

(65) Prior Publication Data

US 2020/0129401 A1 Apr. 30, 2020

(30) Foreign Application Priority Data

Oct. 31, 2018 (JP) .............................. JP2018-205743

(51) Int. Cl.
| | | |
|---|---|---|
| *A61K 8/46* | (2006.01) | |
| *A61K 8/19* | (2006.01) | |
| *A61K 8/81* | (2006.01) | |
| *A61Q 1/10* | (2006.01) | |
| *A45D 34/04* | (2006.01) | |
| *B43K 8/02* | (2006.01) | |
| *B43K 8/03* | (2006.01) | |
| *A61Q 1/02* | (2006.01) | |

(52) U.S. Cl.
CPC .............. *A61K 8/46* (2013.01); *A45D 34/042* (2013.01); *A61K 8/19* (2013.01); *A61K 8/8152* (2013.01); *A61K 8/8176* (2013.01); *A61Q 1/02* (2013.01); *A61Q 1/10* (2013.01); *B43K 8/024* (2013.01); *B43K 8/03* (2013.01); *A61K 2800/43* (2013.01); *A61K 2800/872* (2013.01)

(58) Field of Classification Search
CPC .......... A61K 8/46; A61K 8/19; A61K 8/8152; A61K 8/8176; A61K 2800/43; A61K 2800/872; A45D 34/042; A61Q 1/02; A61Q 1/10; B43K 8/024; B43K 8/03
See application file for complete search history.

(56) References Cited

U.S. PATENT DOCUMENTS

| | | | | |
|---|---|---|---|---|
| 5,688,493 A | * | 11/1997 | Sugawara ............ | A61K 8/0212 424/489 |
| 7,201,527 B2 | * | 4/2007 | Thorpe ................ | A45D 34/042 401/269 |
| 8,362,089 B2 | * | 1/2013 | Hashimoto ............ | A61Q 5/02 514/778 |
| 9,918,909 B2 | * | 3/2018 | Boyd .................... | A61K 8/0283 |
| 10,143,288 B2 | * | 12/2018 | Sakuma ................ | A45D 34/042 |
| 2003/0123922 A1 | * | 7/2003 | Kabayashi ............... | B43K 7/01 401/206 |
| 2008/0160056 A1 | * | 7/2008 | Boyd ....................... | A61Q 11/00 424/401 |
| 2009/0076211 A1 | * | 3/2009 | Yang ..................... | C09D 17/001 524/459 |
| 2017/0042775 A1 | * | 2/2017 | Yamaguchi ............... | A61K 8/11 |

FOREIGN PATENT DOCUMENTS

| | | |
|---|---|---|
| JP | 2004-315459 | 11/2004 |
| JP | 2010-260839 | 11/2010 |
| JP | 2016-087094 | 5/2016 |

* cited by examiner

*Primary Examiner* — Robert A Wax
*Assistant Examiner* — Olga V. Tcherkasskaya
(74) *Attorney, Agent, or Firm* — Soei Patent & Law Firm

(57) ABSTRACT

A water-based liquid cosmetic containing diethylhexyl sodium sulfosuccinate, an inorganic coloring pigment, a water-soluble dispersant, and a film-forming polymer emulsion, wherein a content of diethylhexyl sodium sulfosuccinate is 0.01 to 1 mass % and a content of the inorganic coloring pigment is 3 to 20 mass %, based on a total amount of the cosmetic, and wherein the inorganic coloring pigment contains carbon black.

12 Claims, 1 Drawing Sheet

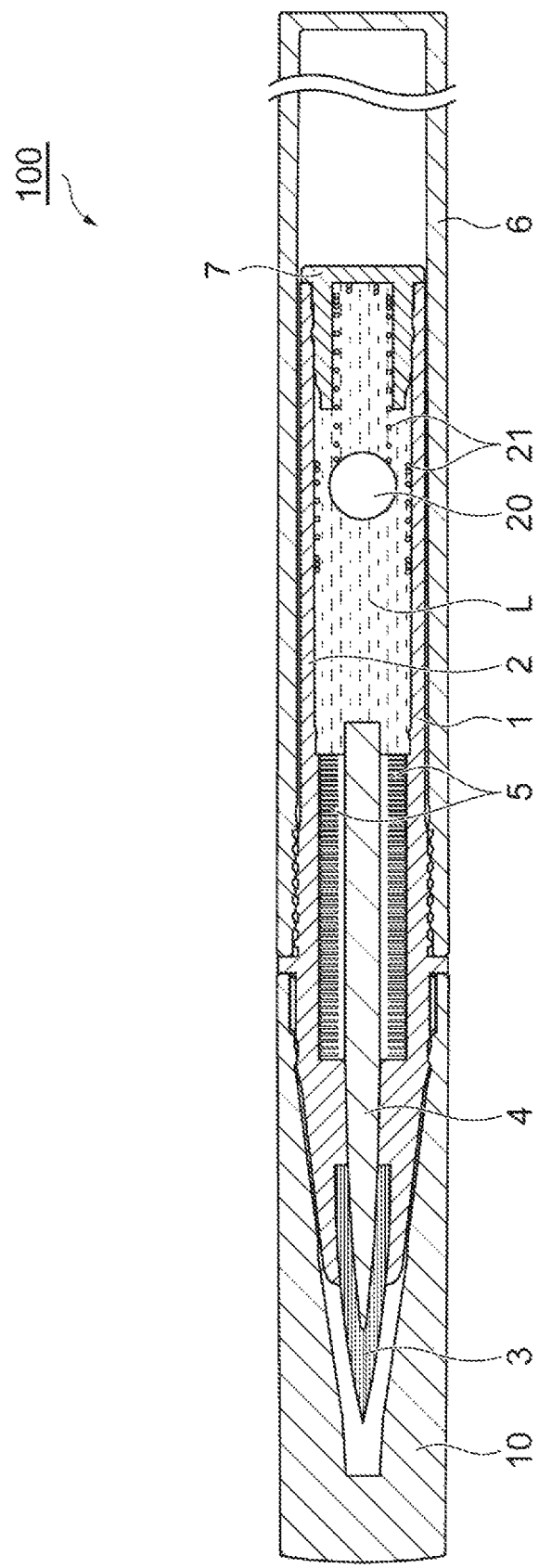

WATER-BASED LIQUID COSMETIC

CROSS-REFERENCE TO RELATED APPLICATIONS

This application claims the benefit of priority from Japanese Patent Application No. 2018-205743, filed on Oct. 31, 2018, the entire contents of which are incorporate herein by reference.

TECHNICAL FIELD

The present application relates to a water-based liquid cosmetic.

BACKGROUND

Water-based liquid cosmetics for use as makeup cosmetics are known to include colorants dissolved or dispersed in water or aqueous organic solvents. Eyeliners and eyebrow cosmetics often use inorganic color pigments as colorants. This is because the eyeliners particularly appear to require deep color line-drawing for the purpose of intensifying the impression of eyes. The inorganic coloring pigments, however, have a large specific gravity; therefore, their aggregation and sedimentation are likely to occur, which results in their insufficient dispersion in the water-based liquid cosmetics to frequently cause irregularities in the line-drawing.

In addition, the water-based cosmetics tend to be poorer in the water resistance and abrasion resistance of cosmetic films than oil-based cosmetics or water-in-oil type cosmetics. Thus, they are the types of formulation that are difficult to enhance makeup durability.

A method for dispersing a powder ingredient in a water-based liquid cosmetic includes compounding a surfactant therein (for example, see Japanese Unexamined Patent Publication No. 2004-315459). In order to enhance the dispersibility of an inorganic coloring pigment, a hydrophilic nonionic surfactant having a high HLB (Hydrophilic Lipophilic Balance) may be used, or alternatively, the amount of a surfactant to be added may be increased. However, these are likely to reduce the water resistance and abrasion resistance of cosmetic films.

From a different standpoint, there has been proposed a technique for improving the water resistance of a water-based liquid cosmetic by compensating for the dispersion of an inorganic coloring pigment with an ingredient other than a surfactant (for example, see Japanese Unexamined Patent Publication No. 2010-260839).

SUMMARY

Water-based cosmetics often experience difficulty in forming uniform cosmetic films because of less adhesion to the skin as compared with oil-based cosmetics or water-in-oil type cosmetics. An eyeliner or an eyebrow cosmetic is usually used on the skin after application of a base makeup, such as a foundation or an eye shadow. In particular, when the skin is coated with an oil-based cosmetic such as an oil-based foundation, it is difficult to draw a uniform line using a water-based cosmetic which tends to be repelled on the skin.

The liquid cosmetic disclosed in Japanese Unexamined Patent Publication No. 2010-260839 attempts to improve the adhesion to the skin and the water resistance by compounding a specific amount of a dispersant made of a film-forming resin. However, the adhesion to the skin and the uniformity of line-drawing on made-up skin are unsatisfactory.

Disclosed herein is a water-based liquid cosmetic which can provide line-drawing of a cosmetic film having sufficient depth of color in combination with sufficient water resistance and abrasion resistance even on the skin already coated with an oil-based cosmetic, the cosmetic film being accompanied by sufficient uniformity and adhesion.

In some examples, the water-based liquid cosmetic comprises diethylhexyl sodium sulfosuccinate, an inorganic coloring pigment, a water-soluble dispersant, and a film-forming polymer emulsion. In some examples, a content of diethylhexyl sodium sulfosuccinate is 0.01 to 1 mass % and a content of the inorganic coloring pigment is 3 to 20 mass %, based on a total amount of the cosmetic, and the inorganic coloring pigment comprises carbon black.

Having the composition described above, the water-based liquid cosmetic can provide line-drawing of a cosmetic film having sufficient depth of color in combination with sufficient water resistance and abrasion resistance even on the skin coated with an oil-based cosmetic, the cosmetic film being accompanied by sufficient uniformity and adhesion.

An example product for liquid cosmetics is a pen type cosmetic product. The pen type cosmetic product may comprise a cosmetic accommodation part, such as a fiber bundle impregnated with a liquid cosmetic or a part filled with a liquid cosmetic, and an application part made of a brush or felt joined thereto. Examples thereof include a mechanical type product from which the liquid cosmetic is forcibly dispensed by application of force to the accommodation part through dialing or clicking and an automatic pen type product from which the liquid cosmetic is dispensed by the action of its surface tension and capillary phenomenon.

The water-based liquid cosmetic may exhibit the above-mentioned effects even if its viscosity has been made low. In this instance, the water-based liquid cosmetic has sufficient dispensability so that even an automatic pen type product can dispense the cosmetic stably. In automatic pen type products, the capillary force and the liquid retention force vary depending on the types of their application parts. Thus, a brush experiences less dispensability than does felt. However, an automatic pen type product having an application part made of brush can still dispense the water-based liquid cosmetic stably.

From the viewpoint of improving the dispersibility of inorganic coloring pigments and the abrasion resistance of a cosmetic film, the aforementioned water-soluble dispersant may comprise at least one water-soluble polymer selected from the group consisting of polyvinylpyrrolidone, polyvinyl alcohol, and an acrylic polymer.

From the viewpoint of the abrasion resistance and water resistance of the cosmetic film, the acrylic polymer may be an alkyl acrylate copolymer.

From the viewpoint of the dispensability, the water-based liquid cosmetic may have a viscosity of 50 mPa·s or less at 25° C.

From the viewpoint of improving the water resistance and abrasion resistance of the cosmetic film, the water-based liquid cosmetic may comprise no nonionic surfactant having an HLB of 8 or more. Or alternatively, a content of any nonionic surfactant having an HLB of 8 or more may be 0.1 mass % or less based on a total amount of the cosmetic.

BRIEF DESCRIPTION OF THE DRAWINGS

FIG. 1 is a schematic cross-sectional view illustrating an example liquid cosmetic container.

DETAILED DESCRIPTION

In the following description, with reference to the drawings, the same reference numbers are assigned to the same components or to similar components having the same function, and overlapping description is omitted.

An example water-based liquid cosmetic comprises diethylhexyl sodium sulfosuccinate, an inorganic coloring pigment, a water-soluble dispersant, and a film-forming polymer emulsion.

In one or more embodiments, the term "water-based" may be understood to mean that at least water is contained in the liquid cosmetic. The water-based cosmetic may further comprise a lower alcohol having 1 to 5 carbon atoms, such as ethanol, in addition to water.

In one or more embodiments, a content of water in the water-based liquid cosmetic may be 40 to 80 mass %, 45 to 80 mass %, or 50 to 80 mass %, based on a total amount of the cosmetic.

In one or more embodiments, the term "liquid" may be understood to refer to one having fluidity at 25° C. A viscosity of the water-based liquid cosmetic may be 10,000 mPa·s or less at 25° C. and may be appropriately set, depending on the form of a container. For example, in the case of a bottle type container, a cosmetic having a viscosity of 10,000 mPa·s or less at 25° C. may be used, while in the case of a pen type container, a cosmetic having a viscosity of 5,000 mPa·s or less at 25° C. may be used.

From the viewpoint of improving dispensability in an automatic pen type product, the water-based liquid cosmetic may have a viscosity of 50 mPa·s or less, 30 mPa·s or less, or 20 mPa·s or less at 25° C. The dispensability may be further improved by employing the cosmetic with a viscosity in one of the increasingly lower ranges disclosed above, such as "20 mPa·s or less." Also, from the viewpoint of usability, the water-based liquid cosmetic may have a viscosity of 2 mPa·s or more, or 3 mPa·s or more at 25° C. The usability may be further improved by employing the cosmetic with a viscosity in the higher range disclosed above.

The viscosity described above refers to a measured value of a sample at 25° C. using a Brookfield viscometer (BM type) under the following conditions:

5 to 50 mPa·s: BL adaptor with a rotational speed of 12 rpm 50 to 500 mPa·s: Rotor No. 1 with a rotational speed of 12 rpm 250 to 2,500 mPa·s: Rotor No. 2 with a rotational speed of 12 rpm 1,000 to 10,000 mPa·s: Rotor No. 3 with a rotational speed of 12 rpm 5,000 to 50,000 mPa·s: Rotor No. 4 with a rotational speed of 12 rpm Diethylhexyl Sodium Sulfosuccinate In one or more embodiments, an aqueous solution comprising diethylhexyl sodium sulfosuccinate (diethylhexyl Na sulfosuccinate) may be used. The diethylhexyl Na sulfosuccinate may be a commercial product such as NIKKOL OTP-75 (product name, manufactured by Nikko Chemicals Co., Ltd.).

In one or more embodiments, a content of diethylhexyl Na sulfosuccinate in the water-based liquid cosmetic may be 0.01 to 1 mass %, 0.05 to 0.8 mass %, 0.1 to 0.8 mass %, or 0.1 to 0.5 mass %, based on a total amount of the cosmetic. A cosmetic which includes the content of diethylhexyl Na sulfosuccinate within the above ranges is excellent in adaptability with the skin and in dispensability when used with an automatic pen type product, for example. These properties may further be improved by including a content of diethylhexyl Na sulfosuccinate at one of the increasingly smaller ranges disclosed above, such as "0.1 to 0.5 mass %."

Inorganic Coloring Pigment

Examples of the inorganic coloring pigment include inorganic coloring pigments that are compounded in cosmetics, and they may be carbon black, black iron oxide, red iron oxide, yellow iron oxide, cobalt oxide, chromium oxide, ultramarine, Prussian blue, titanium oxide, and zinc oxide, for example.

The inorganic coloring pigment may be used alone, or two or more kinds thereof may be used in combination.

In one or more embodiments, a content of the inorganic coloring pigment in the water-based liquid cosmetic may be 3 to 20 mass %, 4 to 20 mass %, or 4 to 15 mass %, based on a total amount of the cosmetic. When the content of the inorganic coloring pigment is within the above ranges, the formation of a cosmetic film that is excellent in the color depth of line-drawing is compatible with the dispersibility and dispensability. These properties may further be improved by including a content of the inorganic coloring pigment at one of the increasingly smaller ranges disclosed above, such as "4 to 15 mass %."

In one or more embodiments, the water-based liquid cosmetic may comprise carbon black as an inorganic coloring pigment. In this instance, carbon black may sufficiently be dispersed in the cosmetic, and a cosmetic film that is excellent in the color depth of line-drawing can be formed uniformly.

In one or more embodiments, a content of carbon black in the water-based liquid cosmetic may be 3 to 20 mass % or 4 to 15 mass %, based on a total amount of the cosmetic. A cosmetic which includes the content of carbon black within the above ranges is excellent in the color depth of line-drawing as well as in dispensability. These properties may further be improved by including in the cosmetic, a content of carbon black at the smaller range disclosed above.

In one or more embodiments, the water-based liquid cosmetic may comprise a colorant other than the inorganic coloring pigment. Dyes, coloring matters, and organic coloring pigments that are compounded in cosmetics may be used as the colorant. Some examples include: dyes, such as Red No. 227, Blue No. 1, Yellow No. 4, and Yellow No. 5; natural coloring matters, such as carmine and safflower; organic coloring pigments, such as Red No. 228, Red No. 226, Blue No. 404, Red No. 202, and Yellow No. 4 aluminum lake; pearl pigments, such as titanium dioxide-coated mica; fish scale foil; and bismuth oxychloride.

In one or more embodiments, the water-based liquid cosmetic may comprise an extender pigment, including silica, glass powder, silicic anhydride, aluminum silicate, magnesium silicate, aluminum magnesium silicate, mica, synthetic mica, synthetic sericite, sericite, talc, kaolin, silicon carbide, barium sulfate, and resin particles such as PMMA (poly methyl methacrylate) particles.

Water-Soluble Dispersant

In one or more embodiments, the water-soluble dispersant may employ, for example, a water-soluble polymer, such as polyvinylpyrrolidone (PVP), polyvinyl alcohol (PVA), or an acrylic polymer; a surfactant such as a hydrophilic nonionic surfactant; an anionic surfactant other than diethylhexyl sodium sulfosuccinate; a cationic surfactant; or an amphoteric surfactant.

Examples of the acrylic polymers include a homopolymer or a copolymer of one or two or more monomers selected from the group consisting of (meth)acrylic acid and an alkyl (meth)acrylate. The alkyl (meth)acrylate may be an alkyl ester having 1 to 4, or 8 carbon atoms. Further, both of the homopolymer and the copolymer may be a water-soluble polymer which contains a structure having an acidic residue in its side chain as a monomer unit structure to constitute a main chain and which can dissolve in water by neutralization. The acrylic polymer may be a neutralized product, such as an ammonium salt.

The acrylic polymer may be compounded in the water-based liquid cosmetic in a form of a mixed solution with water, ethanol, a polyalcohol, or a mixture of the foregoing.

The acrylic polymer may be an alkyl acrylate copolymer. The alkyl acrylate copolymer is sold under the name of Luvimer 100P (manufactured by BASF), COVACRYL A15 (manufactured by Sensient Technologies Corporation, with a solid content of 30 mass %), JURIMER AT-210 and AT-510 (manufactured by TOAGOSEI Co., Ltd., with a solid content of 30 mass %), for example. In one or more embodiments, the term "alkyl acrylate copolymer" may be understood to refer to a copolymer in an alkyl acrylate copolymer, a solution (1) of the alkyl acrylate copolymer, or a solution (2) of the alkyl acrylate copolymer under the Japanese Standards of Quasi-drug Ingredients.

Examples of the hydrophilic nonionic surfactant include a polyoxyalkylene alkyl ether, a glycerol alkyl ether, a glycerol fatty acid ester, a polyglycerol fatty acid ester, a sorbitan fatty acid ester, an alkylene glycol adduct thereof, a polyalkylene glycol fatty acid ester, a polyglycerol-modified silicone, and a polyether-modified silicone. Examples of the anionic surfactant include an alkyl phosphate ester salt, a polyoxyalkylene alkyl ether phosphate salt, a sulfonate salt, an alkyl sulfate salt, and a polyaspartate salt. Examples of the cationic surfactant include an alkylamine salt and an alkyltrimethylammonium salt. Examples of the amphoteric surfactant include lecithin, a carbobetaine-type amphoteric surfactant, a sulfobetaine-type amphoteric surfactant, and an amino acid-type amphoteric surfactant.

In one or more embodiments, the water-based liquid cosmetic may comprise a water-soluble dispersant capable of fainting a film, from the viewpoint of the dispersibility of the inorganic coloring pigment and the abrasion resistance of a cosmetic film. Additionally, the water-soluble dispersant may comprise at least one water-soluble polymer selected from the group consisting of polyvinylpyrrolidone, polyvinyl alcohol, and an acrylic polymer.

The water-soluble dispersant may be used alone, or two or more kinds thereof may be used in combination.

In one or more embodiments, a content of the water-soluble dispersant in the water-based liquid cosmetic may be 0.5 to 5 mass %, 1 to 5 mass %, 1 to 4 mass %, or 1 to 3 mass %, based on a total amount of the cosmetic. When the content of the water-soluble dispersant is within the above ranges, the dispersibility of the inorganic coloring pigment is improved. This improvement may be more apparent by including a content of the water-soluble dispersant in the cosmetic at one of the increasingly smaller ranges disclosed above, such as "1 to 3 mass %."

In one or more embodiments, from the viewpoint of improving the water resistance and the abrasion resistance of a cosmetic film, a content of the nonionic surfactant having an HLB of 8 or more in the water-based liquid cosmetic may be 0.1 mass % or less, 0.09 mass % or less, 0.05 mass % or less, or 0.01 mass % or less, based on a total amount of the cosmetic. Furthermore, the water-based liquid cosmetic may not comprise any nonionic surfactant having an HLB of 8 or more. The above-mentioned properties of the cosmetic may further be improved by including a content of the nonionic surfactant at the increasingly lower ranges to zero as disclosed above. Examples of the surfactant having an HLB of 8 or more include a polyoxyalkylene alkyl ether and a polyalkylene glycol fatty acid ester.

Additionally, from the viewpoint of improving the water resistance and the abrasion resistance of a cosmetic film, a content of any nonionic surfactant in the water-based liquid cosmetic may be 0.1 mass % or less, 0.09 mass % or less, 0.05 mass % or less, or 0.01 mass % or less, based on a total amount of the cosmetic. Furthermore, the water-based liquid cosmetic may not comprise any nonionic surfactant.

Film-Forming Polymer Emulsion

Examples of a polymer contained in the film-forming polymer emulsion include a water-insoluble polymer or copolymer which contains an alkyl (meth)acrylate monomer as structural unit. The copolymer may be a random copolymer, a graft copolymer, a block copolymer, or a core-shell copolymer. The core-shell copolymer may be, for example, an acrylic resin emulsion or a urethane-acrylic composite resin emulsion which contains particles having a core-shell structure wherein the core is an acrylic resin, such as poly(meth)acrylate, or a urethane resin, such as polyurethane, and the shell is an acrylic resin, such as poly(meth)acrylate, or a urethane resin, such as polyurethane.

Examples of the film-foaming polymer emulsion include an alkyl acrylate copolymer emulsion, an alkyl acrylate/styrene copolymer emulsion, an alkyl acrylate/vinyl acetate copolymer emulsion, an alkyl acrylate/diacetone acrylamide copolymer emulsion, and a urethane/acrylic composite resin emulsion. Among these, the alkyl acrylate-styrene copolymer emulsion may provide improved water resistance and abrasion resistance of a cosmetic film. The alkyl acrylate may be understood to encompass an alkyl methacrylate.

In one or more embodiments, the film-forming polymer emulsion may have a solid content of 30 to 60 mass % in water as medium.

The film-forming polymer emulsion may employ a commercial product. The alkyl acrylate copolymer emulsion is sold under the names of YODOSOL GH800F (manufactured by Akzo Nobel Company, with a solid content of 45 mass %), YODOSOL GH810F (manufactured by Akzo Nobel Company, with a solid content of 46 mass %), YODOSOL GH34F (manufactured by Akzo Nobel Company, with a solid content of 42 mass %), and DAITOSOL 5000SJ (manufactured by Daito Kasei Kogyo Co., Ltd., with a solid content of 50 mass %), for example. The alkyl acrylate/styrene copolymer emulsion is sold under the names of YODOSOL GH41F (manufactured by Akzo Nobel Company, with a solid content of 45 mass %), DAITOSOL 5000STY (manufactured by Daito Kasei Kogyo Co., Ltd., with a solid content of 50 mass %), and EMUPOLY CE-119N (available from Nikko Chemicals Co., Ltd.), for example. The alkyl acrylate/vinyl acetate copolymer emulsion is sold under the name of VINYLSOL 2140L (manufactured by Daido Chemical Corporation, with a solid content of 45 mass %), for example. The alkyl acrylate/diacetone acrylamide copolymer emulsion is sold under the name of PLASCIZE L-9540U (a solid content of 40 mass %, manufactured by Goo Chemical Co., Ltd.), for example. The urethane acrylic composite resin emulsion is sold under the name of RIKABOND SS-3000 (a solid content of 30 mass %, manufactured by Japan Coating Resin Co., Ltd.), for example.

The film-forming polymer emulsions may be used alone, or two or more kinds thereof may be used in combination.

In one or more embodiments, a content of the film-forming polymer emulsion in the water-based liquid cosmetic may be 1 to 20 mass %, 2 to 15 mass %, or 4 to 10 mass % as solid content, based on a total amount of the cosmetic. When the content of the film-forming polymer emulsion is within the above ranges, the water resistance and abrasion resistance of a cosmetic film is compatible with the dispensability in an automatic pen type product. These properties may further be improved by including a content of the film-forming polymer emulsion at one of the increasingly smaller ranges disclosed above, such as "4 to 10 mass %." Further, when the content of the film-forming polymer emulsion is set at less than or equal to the aforementioned upper limits, tight skin feeling resulting from an excessively hardened cosmetic film will be avoided.

In one or more embodiments, the water-based liquid cosmetic may comprise, in addition to the respective ingredients described above, other ingredients that are used in cosmetics. For example, any one or more of a moisturizing agent, a viscosity modifier, a preservative, a pH adjuster, a chelating agent, a UV absorber, a vitamin, a beauty ingredient, an antioxidant, and a flavoring agent may be added in such a range that does not impair the effects of the cosmetic.

In one or more embodiments, the water-based liquid cosmetic may be produced by dissolving or dispersing the above-described diethylhexyl sodium sulfosuccinate, inorganic coloring pigment, water-soluble dispersant, film-forming polymer emulsion, and water, and other ingredients, and by stirring and mixing the mixture uniformly.

The water-based liquid cosmetic may be used as a makeup cosmetic, such as an eyeliner, an eyebrow cosmetic, an eyeshadow or a mascara. The improved color depth of line-drawing and usability, for example, makes the cosmetic useful as an eyeliner.

In one or more embodiments, the water-based liquid cosmetic may be utilized in a cosmetic product. Example products include a pen type product and a bottle type product. The pen type product may comprise a cosmetic accommodation part, such as a fiber bundle impregnated with a cosmetic or a part filled with a liquid cosmetic, and an application part comprising a brush or felt joined thereto. Examples of the pen type product include a mechanical type from which the liquid cosmetic is forcibly dispensed through application of force to the accommodation part by dialing or clicking and an automatic pen type from which the liquid cosmetic is dispensed by the action of its surface tension and capillary phenomenon.

From the viewpoint of convenience in use and portability, the water-based liquid cosmetic may be used in an automatic pen type product according to one embodiment. The automatic pen type product may employ a container, such as the liquid cosmetic container disclosed in Japanese Unexamined Patent Publication No. 2016-87094.

FIG. 1 is a schematic cross-sectional view showing an example liquid cosmetic container 100. The overall shape of the liquid cosmetic container 100 resembles a writing tool in an elongated narrow round-bar form. In general, the container comprises a cylindrical container body 1, an accommodation part 2 disposed in the container body 1 so as to accommodate a water-based liquid cosmetic L according to one embodiment, a brush 3 installed at a tip of the container body 1 for the application of the water-based liquid cosmetic L in the accommodation part 2, a shaft-like relay wick 4 disposed in the container body 1 for connecting the inner part of the accommodation part 2 with the brush 3, and a bellows component 5 in an approximately cylindrical shape installed around the relay wick 4. In some examples, a gripping cylinder 6 in a bottomed cylindrical shape is screwed to the container body 1 for detachable installation so that a user holding the container body 1 can easily apply the cosmetic. The shape of the container body 1 may be cylindrical, rectangular, or some other shape.

The container body 1 is formed of PP (polypropylene), for example, and is configured to be a tapered cylindrical shape with a flange. A rear end face of the flange part disposed on an outer peripheral surface of the container body 1 abuts on a front end face of the gripping cylinder 6 screwed into the container body 1. A front end face of the flange part abuts on an open end face of a cap 10 installed on the container body 1. An opening at a rear end of the container body 1 is closed with a bottomed cylindrical tale plug 7 inserted therein.

A bellows component 5 is intended for controlling the flow of the water-based liquid cosmetic L and has a groove (bellows) containing the water-based liquid cosmetic L. A cylindrical rear end part of the bellows component 5 fits in a recess of an inner peripheral face of the container body 1 so that the bellows component 5 is installed within the container body 1. The accommodation part 2 is formed between the rear end part of the bellows component 5 and the tail plug 7, and the water-based liquid cosmetic L is accommodated in the accommodation part 2.

The relay wick 4 is, for example, formed of an acrylic resin and extends in the axial direction to pass through a cylinder hole of the bellows component 5. A tip of the relay wick 4 fits into a tip of the bellows component 5 so that the relay wick 4 is installed within the bellows component 5. The relay wick 4 connects the inner part of the accommodation part 2 to the brush 3, while its rear end part enters into the inner part of the accommodation part 2 and its front end part enters into the brush 3. The relay wick 4 allows the water-based liquid cosmetic L to be sucked from the accommodation part 2 by capillary phenomenon and to be supplied to the brush 3.

The brush serves as an applicator in the liquid cosmetic container 100 shown in FIG. 1 but it may be replaced by a felt tip or a urethane tip.

The bottomed cylindrical cap 10 is detachably installed at the tip of the container body 1 by fitting to protect the brush 3.

The accommodation part 2 of the liquid cosmetic container 100 accommodates a stirring element 20 that is movable in the axial direction and a coil spring 21 that is extendable in the axial direction, together with the water-based liquid cosmetic L. In FIG. 1, the stirring element 20 is depicted as a sphere; however, the element may be a polyhedron, a cone or other shape depending on the particular application.

A coil spring 21 is an integrally formed spring including a plurality of spring parts having different diameters (e.g., two spring parts having different diameters as illustrated in FIG. 1) integrally connected in the axial direction, which may be formed of SUS (Steel Use Stainless), for example. The coil spring 21 comprises a small-diameter spring part having a diameter smaller than that of the stirring element 20 in a rear half part thereof and a large-diameter spring part having a diameter larger than that of the stirring element 20 continuously, the latter of which spring parts is adjacent to the forward axial direction of the small-diameter spring.

When the container 100 is shaken by a user, the stirring element 20 that is movable in the axial direction in the large-diameter spring of the coil spring 21 moves in the axial direction. Thus, the water-based liquid cosmetic L is stirred by the movement of the stirring element 20.

In the liquid cosmetic container 100 thus configured, the water-based liquid cosmetic L in the accommodation part 2 flows toward the brush 3 at a front side of the container through the rely wick 4, whereby it is provided to a user for application with the brush 3. The water-based liquid cosmetic container 100 includes the stirring element 10 and the coil spring 21, thereby allowing the water-based liquid cosmetic L to efficiently flow toward the brush 3. This configuration may be changed such that it neither includes the stirring element 10 nor the coil spring 21.

An example automatic pen type container that may utilize the water-based liquid cosmetic has been described above by referring to the liquid cosmetic container 100 having a so-called direct liquid type structure. However, other types of structures may be used. For example, a container having a so-called wadding structure may be used, which omits the bellows components 5, the stirring element 20 and the coil spring 21 in the liquid cosmetic container 100 and which has an accommodation part 2 accommodating a wadding component impregnated with the water-based liquid cosmetic L and sucks the water-based liquid cosmetic L therefrom to supply to the brush 3 through a rear end part of the relay wick 4 entering into an inner part of the wadding component.

ADDITIONAL EXAMPLE EMBODIMENTS

Hereinafter, details of various example embodiments will be described with reference to comparative examples.
Production of Water-Based Liquid Cosmetics

Examples 1 to 15 and Comparative Examples 1 to 8

The respective ingredients shown in Tables 1 to 3 were mixed with a disperser at the ratios (mass %) shown in the corresponding tables to obtain each of the water-based liquid cosmetics. The values for a water-soluble polymer and a polymer emulsion in the tables are, respectively, the amounts of a water-soluble dispersant and a film-forming emulsion to be compounded.

The respective ingredients shown in Tables 1 to 3 employed those described below.

Water-soluble polymer 1: alkyl acrylate copolymer (solid content of 30 mass %)

Polymer emulsion 1: alkyl acrylate/styrene copolymer emulsion (product name "DAITOSOL 5000STY," manufactured by Daito Kasei Kogyo Co. Ltd., with a solid content of 50 mass %)

Polymer emulsion 2: alkyl acrylate copolymer emulsion (product name "DAITOSOL 5000SJ," manufactured by Daito Kasei Kogyo Co. Ltd., with a solid content of 50 mass %)

Evaluation of Water-Based Liquid Cosmetics

The thus-obtained water-based liquid cosmetic was filled in the accommodation part of an automatic type container having the same configuration as the container shown in FIG. 1 (applicator: brush; relay wick: acrylic resin) to prepare a filled product.

Each of the prepared, filled products was evaluated for dispensability, applied condition, abrasion resistance, and water resistance according to the evaluation method described below. In Example 15, a bottle container was filled with a water-based liquid cosmetic and its properties other than the dispensability were evaluated.

Evaluation of Dispensability

A line with a length of about 5 cm was drawn on an arm, and the condition of line-drawing was evaluated for the dispensability according to the following criteria.

(Evaluation Criteria)
A: Sufficiently dispensed, accompanied by deep color line-drawing
B: Dispensed without any problem
C: Insufficiently dispensed
D: Dispensing was problematic with the occurrence of blurs.

Applied Condition on Skin (1)

The cosmetic was applied on an arm, and after drying for 10 minutes, the applied condition was visually observed and evaluated according to the following criteria.

(Evaluation Criteria)
A: Uniform line-drawing without any occurrence of cissing (Extremely good)
B: Nearly uniform line-drawing with almost no occurrence of cissing (Good)
C: A little unevenness in line-drawing with some occurrence of cissing (Slightly poor)
D: Uneven line-drawing with the occurrence of cissing (Poor)

Applied Condition on Skin (2)

The cosmetic was applied on an arm coated with an oil-based foundation having a composition described below, and after drying for 10 minutes, the applied condition was visually observed and evaluated according to the following criteria.

(Evaluation Criteria)
A: Uniform line-drawing without any occurrence of cissing (Extremely good)
B: Nearly uniform line-drawing with almost no occurrence of cissing (Good)
C: A little unevenness in line-drawing with some occurrence of cissing (Slightly poor)
D: Uneven line-drawing with the occurrence of cissing (Poor)

| Composition of Oil-Based Foundation | |
| --- | --- |
| Ingredient | Composition (mass %) |
| Methylpolysiloxane | 20 |
| 2-Ethylhexyl palmitate | 20 |
| Polyethylene wax | 6 |
| Talc | 5 |
| Nylon powder | 4 |
| Heavy liquid isoparaffin | 4 |
| Microcrystalline wax | 3 |
| Vaseline | 3 |
| Sorbitan sesquiisostearate | 2 |
| Crosslinked methylpolysiloxane | 1 |
| Natural vitamin E | as needed (q.l.) |
| Mica | balance (q.s.) |
| Iron oxide | 3 |
| Titanium oxide | 25 |

Evaluation of Abrasion Resistance

The cosmetic was applied on an arm, and after drying for 10 minutes, the arm was rubbed with a fingertip. The residual level of the applied cosmetic was visually observed and evaluated for the abrasion resistance according to the following criteria.

(Evaluation Criteria)
A: No peeling of the applied section (Extremely good)
B: Slight peeling of the applied section (Good)
C: Some peeling of the applied section (Slightly poor)
D: Severe peeling of the applied section (Poor)

Evaluation of Water Resistance

The cosmetic was applied on an arm, and after drying for 10 minutes, the arm was wetted with running water, and rubbed with a finger pulp. The residual level of the applied cosmetic was visually observed and evaluated for the abrasion resistance according to the following criteria.

Evaluation Criteria
A: No peeling of the applied section (Extremely good)
B: Slight peeling of the applied section (Good)
C: Some peeling of the applied section (Slightly poor)
D: Severe peeling of the applied section (Poor)

Viscosity of Water-Based Liquid Cosmetics

The viscosity of a sample was measured at 25° C. using a Brookfield viscometer (BM type) under the following conditions. The measurement time was set at one minute.

5 to 50 mPa·s: BL adaptor with a rotational speed of 12 rpm
50 to 500 mPa·s: Rotor No. 1 with a rotational speed of 12 rpm
250 to 2,500 mPa·s: Rotor No. 2 with a rotational speed of 12 rpm
1,000 to 10,000 mPa·s: Rotor No. 3 with a rotational speed of 12 rpm
5,000 to 50,000 mPa·s: Rotor No. 4 with a rotational speed of 12 rpm

TABLE 1

|  |  | Example 1 | Example 2 | Example 3 | Example 4 | Example 5 | Example 6 | Example 7 | Example 8 |
|---|---|---|---|---|---|---|---|---|---|
| Anionic surfactant | Diethylhexyl Na sulfosuccinate | 0.1 | 0.4 | 0.8 | 0.4 | 0.1 | 0.4 | 0.8 | 0.4 |
|  | Na methyl cocoyl taurate | — | — | — | — | — | — | — | — |
| Inorganic coloring pigment | Carbon black | 8 | 8 | 8 | 8 | 8 | 8 | 8 | 4 |
|  | Prussian blue | — | — | — | — | — | — | — | — |
| Water-soluble dispersant | PVP | 1 | 1 | 1 | 1 | — | — | — | — |
|  | Water-soluble polymer 1 | — | — | — | — | 8 | 8 | 8 | 4 |
| Film-forming polymer emulsion 1 | Polymer emulsion 1 | 10 | 10 | 10 | — | 10 | 10 | 10 | 10 |
|  | Polymer emulsion 2 | — | — | — | 10 | — | — | — | — |
| Moisturizing agent | BG | 10 | 10 | 10 | 10 | 10 | 10 | 10 | 10 |
| Alcohol | Ethanol | 3 | 3 | 3 | 3 | 3 | 3 | 3 | 3 |
| Powder other than coloring pigment | Mica | — | — | — | — | — | — | — | — |
| pH Adjuster | Citric acid | 0.05 | 0.05 | 0.05 | — | — | — | — | — |
|  | Potassium hydroxide | — | — | — | 0.05 | — | — | — | — |
| Viscosity modifier | Xanthan gum | — | — | — | — | — | — | — | — |
|  | Preservative | q.l. | q.l. | q.l. | q.l. | q.l. | q.l. | q.l. | q.l |
|  | Purified water | q.s. | q.s. | q.s. | q.s. | q.s. | q.s. | q.s. | q.s. |
| Evaluation | Dispensability | B | A | A | A | B | A | A | A |
|  | Applied condition on skin (1) | B | B | A | B | A | A | A | A |
|  | Applied condition on skin (2) | B | B | A | B | B | A | A | A |
|  | Abrasion resistance | B | B | B | B | A | A | A | A |
|  | Water resistance | B | B | B | B | A | A | B | B |
|  | Viscosity (mPa · s) | 7 | 7 | 7 | 7 | 6 | 6 | 6 | 4 |

TABLE 2

|  |  | Example 9 | Example 10 | Example 11 | Example 12 | Example 13 | Example 14 | Example 15 |
|---|---|---|---|---|---|---|---|---|
| Anionic surfactant | Diethylhexyl Na sulfosuccinate | 0.4 | 0.4 | 0.1 | 0.4 | 0.8 | 0.4 | 0.4 |
|  | Na methyl cocoyl taurate | — | — | — | — | — | — | — |
| Inorganic coloring pigment | Carbon black | 15 | 8 | 4 | 4 | 4 | 4 | 8 |
|  | Prussian blue | — | — | 4 | 4 | 4 | 4 | — |
| Water-soluble dispersant | PVP | — | — | 1 | 1 | 1 | 1 | 1 |
|  | Water-soluble polymer 1 | 15 | 8 | 1.5 | 1.5 | 1.5 | 1.5 | — |
| Film-forming polymer emulsion-1 | Polymer emulsion 1 | 10 | — | 10 | 10 | 10 | — | 20 |
|  | Polymer emulsion 2 | — | 10 | — | — | — | 10 | — |
| Moisturizing agent | BG | 10 | 10 | 10 | 10 | 10 | 10 | 10 |
| Alcohol | Ethanol | 3 | 3 | 3 | 3 | 3 | 3 | 3 |
| Powder other than coloring pigment | Mica | — | — | — | — | — | — | 5 |
| pH Adjuster | Citric acid | — | — | — | — | — | — | — |
|  | Potassium hydroxide | — | — | — | — | — | 0.05 | — |
| Viscosity modifier | Xanthan gum | — | — | — | — | — | — | 0.5 |
|  | Preservative | q.l. | q.l. | q.l. | q.l. | q.l. | q.l. | q.l. |
|  | Purified water | q.s. | q.s. | q.s. | q.s. | q.s. | q.s. | q.s |

TABLE 2-continued

|  |  | Example 9 | Example 10 | Example 11 | Example 12 | Example 13 | Example 14 | Example 15 |
|---|---|---|---|---|---|---|---|---|
| Evaluation | Dispensability | B | A | B | A | A | A | — |
|  | Applied condition on skin (1) | A | A | A | A | A | A | A |
|  | Applied condition on skin (2) | A | A | B | A | A | A | A |
|  | Abrasion resistance | A | B | A | A | A | B | A |
|  | Water resistance | B | B | A | A | B | B | A |
|  | Viscosity (mPa·s) | 14 | 6 | 5 | 5 | 5 | 5 | 4000 |

TABLE 3

|  |  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Anionic surfactant | Diethylhexyl Na sulfosuccinate | — | — | — | 2 | 0.4 | — | — | 0.4 |
|  | Na methyl cocoyl taurate | — | — | — | — | — | 0.4 | — | — |
| Inorganic coloring pigment | Carbon black | 8 | 4 | 8 | 8 | 20 | 8 | 8 | 8 |
|  | Prussian blue | — | 4 | — | — | — | — | — | — |
| Water-soluble dispersant | PVP | 1 | 1 | — | — | — | — | — | — |
|  | Water-soluble polymer-1 | — | 1.5 | 8 | 8 | 8 | 8 | — | — |
| Film-forming polymer emulsion 1 | Polymer emulsion 1 | 10 | 10 | 10 | 10 | 10 | 10 | 10 | 10 |
|  | Polymer emulsion 2 | — | — | — | — | — | — | — | — |
| Nonionic surfactant | Polyoxyethylene behenyl ether | — | — | — | — | — | — | 2.5 | 2.5 |
| Moisturizing agent | BG | 10 | 10 | 10 | 10 | 10 | 10 | 10 | 10 |
| Alcohol | Ethanol | 3 | 3 | 3 | 3 | 3 | 3 | 3 | 3 |
| Powder other than coloring pigment | Mica | — | — | — | — | — | — | — | — |
| pH Adjuster | Citric acid | 0.05 | — | — | — | — | — | 0.05 | 0.05 |
|  | Potassium hydroxide | — | — | — | — | — | — | 0.05 | 0.05 |
| Viscosity modifier | Xanthan gum | — | — | — | — | — | — | — | — |
|  | Preservative | q.l. | q.l. | q.l. | q.l. | q.l. | q.l. | q.l. | q.l. |
|  | Purified water | q.s. | q.s. | q.s. | q.s. | q.s. | q.s. | q.s. | q.s. |
| Evaluation | Dispensability | C | C | C | B | D | A | C | B |
|  | Applied condition on skin (1) | D | D | D | B | C | A | D | A |
|  | Applied condition on skin (2) | D | D | D | B | C | A | D | B |
|  | Abrasion resistance | B | A | A | D | A | C | D | D |
|  | Water resistance | B | A | A | D | A | C | D | D |
|  | Viscosity (mPa·s) | 7 | 5 | 6 | 6 | 21 | 6 | 5 | 5 |

Example 16: Water-Based Liquid Eyeliner

| | Ingredient | Composition (mass %) |
|---|---|---|
| 1. | Diethylhexyl Na sulfosuccinate | 0.4 |
| 2. | Carbon black | 8 |
| 3. | Alkyl acrylate copolymer solution (solid content of 30 mass %) | 8 |
| 4. | Urethane-acrylic composite resin emulsion (solid content of 30 mass %) | 20 |
| 5. | 1,3-Butylene glycol | 10 |
| 6. | Ethanol | 3 |
| 7. | Preservative | as needed (q.l.) |
| 8. | Purified water | balance (q.s.) |

Production Method

Ingredients 1 to 8 were mixed with a disperser to obtain a water-based liquid eyeliner.

Evaluation

The water-based liquid eyeliner thus obtained was evaluated in the same manner as that described above. With respect to the results, the dispensability was rated as "A," the applied condition on the skin (1) was rated as "A," the applied condition on the skin (2) as "A," the abrasion resistance as "B," and the water resistance as "B." The viscosity of the water-based liquid eyeliner was 7 mPa·s.

Example 17: Water-Based Liquid Eyebrow Cosmetic

| | Ingredient | Composition (mass %) |
|---|---|---|
| 1. | Diethylhexyl Na sulfosuccinate | 0.3 |
| 2. | Carbon black | 3 |
| 3. | Red No. 227 | 0.05 |
| 4. | Yellow No. 4 | 0.1 |
| 5. | Blue No. 1 | 0.02 |
| 6. | PVP | 0.4 |
| 7. | Polymer emulsion D1 (solid content of 50 mass %) | 15 |
| 8. | 1,3-Butylene glycol | 10 |

-continued

| Ingredient | Composition (mass %) |
|---|---|
| 9. Ethanol | 3 |
| 10. Preservative | as needed (q.l.) |
| 11. Purified water | balance (q.s.) |

Production Method

Ingredients 1 to 11 were mixed with a disperser to obtain a water-based eyebrow cosmetic.

Evaluation

The water-based liquid eyebrow cosmetic thus obtained was evaluated in the same manner as that described above. With respect to the results, the dispensability was rated as "A," the applied condition on the skin (1) was rated as "A," the applied condition on the skin (2) as "A," the abrasion resistance as "B," and the water resistance as "B." The viscosity of the water-based liquid eyebrow cosmetic was 4 mPa·s.

It is to be understood that not all aspects, advantages and features described herein may necessarily be achieved by, or included in, any one particular embodiment. Indeed, having described and illustrated various embodiments herein, it should be apparent that other embodiments may be modified in composition and detail. We claim all modifications and variations coming within the spirits and scope of the subject matter claimed herein.

What is claimed is:

1. A pen shaped cosmetic product comprising:
   a water-based liquid cosmetic;
   a cosmetic accommodation part accommodating the water-based liquid cosmetic; and
   an application part for applying the water-based liquid cosmetic on a skin surface, the application part joined to the cosmetic accommodation part and comprising a brush or felt,
   wherein the water-based liquid cosmetic comprises a mixture of:
     a film-forming polymer emulsion;
     diethylhexyl sodium sulfosuccinate;
     an inorganic coloring pigment; and
     a water-soluble dispersant,
   wherein the film-forming polymer emulsion is a polymer emulsion selected from the group consisting of an alkyl acrylate copolymer emulsion, an alkyl acrylate/styrene copolymer emulsion, an alkyl acrylate/vinyl acetate copolymer emulsion, an alkyl acrylate/diacetone acrylamide copolymer emulsion, and a urethane/acrylic composite resin emulsion,
   wherein a content of the diethylhexyl sodium sulfosuccinate is 0.01 to 1 mass % and a content of the inorganic coloring pigment is 3 to 20 mass %, based on a total amount of the cosmetic,
   wherein the inorganic coloring pigment comprises carbon black,
   wherein the film-forming polymer emulsion, the diethylhexyl sodium sulfosuccinate, the inorganic coloring pigment, and the water-soluble dispersant are dissolved or dispersed in the cosmetic, and
   wherein the cosmetic comprises no more than 0.1 mass % of a nonionic surfactant, based on the total amount of the cosmetic.

2. The pen shaped cosmetic product according to claim 1, wherein the water-soluble dispersant comprises at least one water-soluble polymer selected from the group consisting of polyvinylpyrrolidone, polyvinyl alcohol, and an acrylic polymer.

3. The pen shaped cosmetic product according to claim 1, wherein the water-soluble dispersant comprises at least one water-soluble polymer including an alkyl acrylate copolymer.

4. The pen shaped cosmetic product according to claim 1, wherein the water-based liquid cosmetic has a viscosity of 50 mPa·s or less at 25° C.

5. The pen shaped cosmetic product according to claim 1, wherein a content of the water-soluble dispersant is 0.5 to 5 mass % based on the total amount of the cosmetic.

6. The pen shaped cosmetic product according to claim 1, wherein a content of the film-forming polymer emulsion is 1 to 20 mass % as a solid content concentration based on the total amount of the cosmetic.

7. The pen shaped cosmetic product according to claim 1, wherein the pen shaped cosmetic product is an automatic pen shaped cosmetic product from which the liquid cosmetic is dispensed by a combination of surface tension and capillary action.

8. A pen shaped cosmetic product comprising:
   a water-based liquid cosmetic;
   a cosmetic accommodation part accommodating the water-based liquid cosmetic; and
   an application part for applying the water-based liquid cosmetic on a skin surface, the application part joined to the cosmetic accommodation part and comprising a brush or felt,
   wherein the water-based liquid cosmetic comprises a mixture of:
     1 to 20 mass % of a film-forming polymer emulsion as a solid content concentration;
     0.01 to 1 mass % of diethylhexyl sodium sulfosuccinate;
     3 to 20 mass % of an inorganic coloring pigment;
     0.5 to 5 mass % of a water-soluble dispersant; and
     40 to 80 mass % of water, based on a total amount of the cosmetic,
   wherein the film-forming polymer emulsion is a polymer emulsion selected from the group consisting of an alkyl acrylate copolymer emulsion, an alkyl acrylate/styrene copolymer emulsion, an alkyl acrylate/vinyl acetate copolymer emulsion, an alkyl acrylate/diacetone acrylamide copolymer emulsion, and a urethane/acrylic composite resin emulsion,
   wherein the inorganic coloring pigment comprises carbon black,
   wherein the film-forming polymer emulsion, the diethylhexyl sodium sulfosuccinate, the inorganic coloring pigment, and the water-soluble dispersant are dissolved or dispersed in the cosmetic, and
   wherein the cosmetic comprises no more than 0.1 mass % of a nonionic surfactant, based on the total amount of the cosmetic.

9. The pen shaped cosmetic product according to claim 8, wherein the water-soluble dispersant comprises at least one water-soluble polymer selected from the group consisting of polyvinylpyrrolidone, polyvinyl alcohol, and an acrylic polymer.

10. The pen shaped cosmetic product according to claim 8, wherein the water-soluble dispersant comprises at least one water-soluble polymer including an alkyl acrylate copolymer.

11. The pen shaped cosmetic product according to claim 8, wherein the water-based liquid cosmetic has a viscosity of 50 mPa·s or less at 25° C.

12. The pen shaped cosmetic product according to claim 8, wherein the pen shaped cosmetic product is an automatic pen shaped cosmetic product from which the liquid cosmetic is dispensed by a combination of surface tension and capillary action.

* * * * *